United States Patent
Andersson

(10) Patent No.: US 6,824,453 B1
(45) Date of Patent: Nov. 30, 2004

(54) SURFACE TREATMENT NOZZLE

(75) Inventor: Göran Andersson, Nynäshamn (SE)

(73) Assignee: Amdent AB, Nynashamn (SE)

( * ) Notice: Subject to any disclaimer, the term of this patent is extended or adjusted under 35 U.S.C. 154(b) by 12 days.

(21) Appl. No.: 10/088,873

(22) PCT Filed: Sep. 20, 2000

(86) PCT No.: PCT/SE00/01825

§ 371 (c)(1),
(2), (4) Date: Jun. 25, 2002

(87) PCT Pub. No.: WO01/21087

PCT Pub. Date: Mar. 29, 2001

(30) Foreign Application Priority Data

Sep. 22, 1999 (SE) .............................................. 9903419

(51) Int. Cl.7 ................................................. B24C 5/04
(52) U.S. Cl. ............................. 451/102; 451/36; 451/38
(58) Field of Search ........................... 433/119, 86, 88; 451/39, 38, 40, 99, 102, 90, 36

(56) References Cited

U.S. PATENT DOCUMENTS

| | | | |
|---|---|---|---|
| 3,972,123 A | 8/1976 | Black | |
| 4,174,571 A | 11/1979 | Gallant | |
| 4,412,402 A | * 11/1983 | Gallant | ........................ 451/40 |
| 4,696,644 A | 9/1987 | Goof | |
| 4,950,160 A | 8/1990 | Karst | |
| 5,509,849 A | * 4/1996 | Spears, Jr. | ..................... 451/40 |
| 6,139,320 A | * 10/2000 | Hahn | ......................... 433/119 |
| 6,203,406 B1 | * 3/2001 | Rose et al. | .................... 451/39 |
| 6,287,180 B1 | * 9/2001 | Hertz | .......................... 451/90 |

* cited by examiner

Primary Examiner—Lee D. Wilson
(74) Attorney, Agent, or Firm—Young & Thompson

(57) ABSTRACT

There is described a surface treatment nozzle which generates a surface treatment jet that comprises a suspension of surface treatment material and gas and a surrounding liquid-containing jet for preventing dusting. The surface treatment jet has a high velocity compared with the velocity of solely liquid and is conveyed in an inner tube (13; 31) and the liquid is conveyed in a channel (12) between the inner tube and a tube (11) concentrically surrounding the inner tube. There is included a mixing arrangement (14, 15, 16; 22; 29, 30, 25) for mixing the liquid with gas upstream of the nozzle outlet and to impart to the liquid/gas mixture a velocity in the same order of magnitude as the velocity of the surface treatment jet at said outlet.

14 Claims, 4 Drawing Sheets

SURFACE TREATMENT NOZZLE

BACKGROUND OF THE INVENTION

Teeth are often polished with the aid of polishing nozzles that blow a polishing mixture of air and powder against the tooth to be polished. The powder is most often bicarbonate. Another gas can be used instead of air. Jets of water that form a curtain around the powder/air suspension are also sprayed onto the tooth to prevent dusting.

The principle developed in accordance with the invention is not restricted solely to polishing operations, but can also be applied with other types of powder, such as $Al_2O_3$ for instance, to abrade a tooth in scaling an outer surface of the tooth, or can be applied instead of conventional drilling. A small polishing and drilling nozzle may, of course, also be used in contexts other than with teeth, for instance in connection with manicures, the production of jewellery, and the like.

A number of different systems in which the aforesaid principle is used are known to the art. For instance, U.S. Pat. Nos. 3,972,123, 4,174,571 and 4,696,644 teach a tooth-polishing nozzle which includes mutually concentric tubes of which the centre tube conveying the powder/air suspension projects in relation to the outermost tube, wherein water is conveyed in a channel defined between both tubes. U.S. Pat. No. 4,412,402 describes a more functional design where the centremost tube carrying the powder/air suspension is withdrawn in relation to the water-conveying outer tube. In addition, the faster flowing powder/air suspension is able to entrain at least a part of the much slower water flow, up to the orifice of the polishing nozzle.

One problem with earlier designs is that the powder/air suspension has a rate of flow of about 15–20 ml/min., while only a total flow of water of 5–15 ml/min. can be achieved. It will be noted that the lowest possible water flow is desired, so that the patient will not feel that he is drowning in water and so that not too much water will be applied to the surface of the tooth being polished. Powder particles will then be deposited in the water instead of on the tooth. This means that the air velocity $v_{air}$ will be about 1000 to 1500 times the water velocity $v_{water}$. Although it is true that some water will be entrained by the air in the device described in U.S. Pat. No. 4,412,402 in particular, the effect achieved therewith is in no way satisfactory. Furthermore, there is a significant imbalance between ejection of the powder/air suspension and the water, due to the different velocities, which gives rise to turbulence and vigorous mixing between the flows.

SUMMARY OF THE INVENTION

One object of the invention is to provide a surface treatment nozzle which functions to eject powder/gas and a liquid-containing protective curtain, where said ejections have the least possible effect on one another.

Another object of the invention is to provide a surface treatment nozzle that ejects powder/gas and a liquid-containing protective curtain where but small turbulence is obtained between the different flows.

Another object of the invention is to provide a surface treatment nozzle that includes but few separate parts and is readily manufactured.

The invention thus relates to an improved surface treatment nozzle for generating a surface treatment jet comprising a suspension of surface treatment material and gas and a liquid-containing surrounding jet for preventing "dusting", wherein the surface treatment jet has a greater velocity than the velocity of solely liquid, wherein the surface treatment jet is conveyed in an inner tube and the liquid in a channel located between said inner tube and a tube that surrounds the inner tube concentrically. According to the invention, there is provided a mixing arrangement for mixing liquid with gas upstream of the nozzle outlet and imparting to the liquid/gas suspension a velocity of the same order of magnitude as the velocity of the surface treatment jet at said outlet.

The mixing arrangement will preferably include an internal outlet from the liquid conveying channel and discharge means for delivering part of the gas in the surface treatment jet, as gas for producing the gas/liquid mixture in an amount such as to impart the desired velocity thereto. The mixing arrangement may include an expansion channel for the liquid and gas mixture externally of the discharge means. The mixing arrangement will preferably include an at least internal constriction of the inner tube downstream of the discharge means.

The inner tube that conveys the surface treatment material/gas suspension may be circular at least at the nozzle orifice and have a diameter which provides space for a surrounding flow of the liquid/gas mixture through cavities around the orifice of the inner tube. The cavities around the orifice of the inner tube may comprise a ring of drilled holes or a central irregular hole that includes wall parts which provide internal support for the orifice of said inner tube when said tube is inserted in the central hole.

The inner tube (13; 31) conveying the suspension of surface treatment material and gas may have a polygonal orifice (28), e.g., an orifice with three corners, at least up to the nozzle orifice, and the nozzle orifice may have a central round hole (27) with a diameter adapted as a corner support and to provide space for a surrounding flow of liquid and gas mixture through said cavities around the orifice (28) of the inner tube. The sizes and forms of the discharge means, the expansion channel, the inner constriction and the cavities through which the liquid/gas mixture exits should be balanced in relation to each other such as to achieve the best possible similarity between the respective velocities of the suspension of surface treatment material and gas and the mixture of liquid and gas. The gas may be air and the surface treatment material may be a polishing material, for instance bicarbonate, or an abrasive material, for instance $Al_2O_3$.

Because the velocities of both ejected flows lie in the same order of magnitude, there is practically no turbulence between the flows at the outlet orifice of the surface treatment nozzle. Reduced turbulence results in improved efficiency and also in small inter-mixing between the flow areas.

BRIEF DESCRIPTION OF THE DRAWINGS

The invention will now be described with reference to the accompanying drawings, which are only to be considered as exemplifications of the inventive principle, wherein.

Those components that find correspondence in the various Figures have been identified with the same reference signs.

DESCRIPTION OF THE PREFERRED EMBODIMENTS

Figure 1:
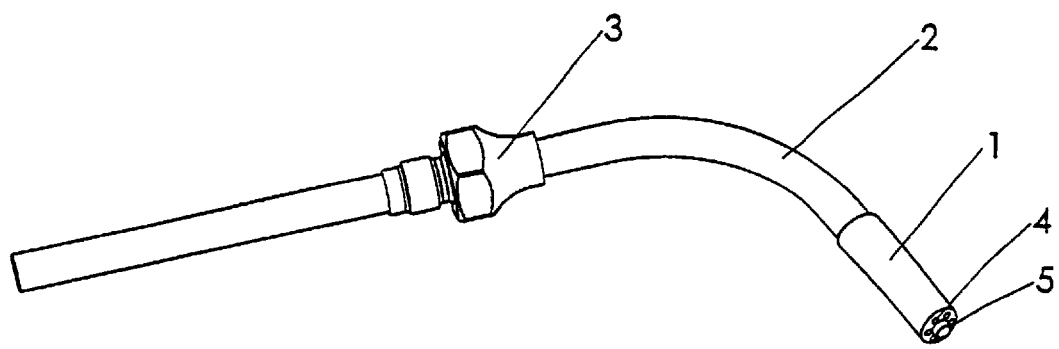
FIG. 1 is an overall view of a surface treatment instrument.

Shown in FIG. 1 is an inventive surface treatment head 1 in which an inner concentric tube extends throughout the entire instrument. The concentric tubes (not shown in FIG. 1) have a curve or bend 2 close to the head 1 in order to provide the operator with a good working position, i.e. for the dentist or dental hygienist in the case of dental treatment. The illustrated bead includes an inner hexagonal support 3 for a handle (not shown) inserted over the rear part of the instrument. Means for delivering powder/gas suspension to the inner tube and liquid to the space between the concentric tubes are disposed at the rear end of the instrument. This supply is achieved with the aid of known technology and constitutes no part of the actual invention and is therefore not shown. The gas is preferably air and the surface treatment jet is hereinafter referred to as the powder/air suspension. The liquid is preferably water and is therefore referred to as such hereinafter.

According to the principle of the invention, water and air are intermixed in the surface treatment head prior to ejecting the mixture through openings 4 in one end of the head, in the form of a curtain around the powder/air suspension, which is ejected as polishing agent through a central opening 5 in the outer end of the head 1. The respective ejected water/air and powder/air suspensions shall have mutually the same velocities, such that one mixture shall not be required to entrain the other mixture in order to prevent turbulence and intermixing between the flow areas. This type of arrangement provides a splendid function, since the forcibly ejected water/air mixture forms a water mist. Tests have shown that the invention functions very satisfactorily in a highly dust-free manner.

It thus lies within the scope of the invention to deliver a water/air mixture to the outer tube right from the connection source. However, this is rather impracticable as the hose arrangement will then be clumsy. In practice, the function of the invention is improved when the water/air mixture is delivered relatively close to the outlet orifice of the polishing nozzle and air contained in the powder/air suspension is used as an admixture in the water. This also enables the suspension and mixture to be given the same velocity more easily.

Figure 2:
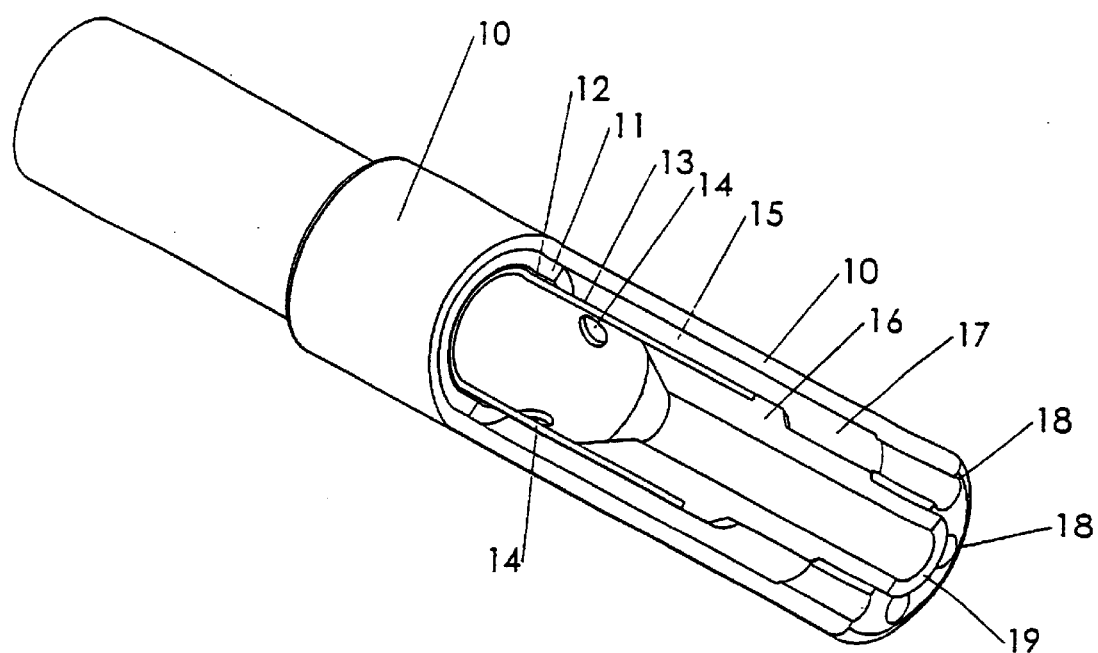
FIG. 2 illustrates in perspective and partially in section a first embodiment of a surface treatment head according to the invention.

The embodiment shown in FIG. 2 includes an outermost protective tube 10, followed by an outer tube 11 which defines part of a water channel 12, and an inner tube 13 which functions to define a further part of the water channel 12 and also as powder/air suspension delivery tube. The outer tube 11 terminates at a relatively long distance upstream of the front end of the protective tube 10. The tubes 11 and 13 lie close together at the rear part, such as to define therebetween a relatively narrow water channel, said water having a low rate of flow in said channel, e.g., a flow rate of 5–15 ml/min. The tube 13 is provided downstream of the end of the outer tube 11 with a number of through-penetrating holes 14 which thus open into the wider channel 15 defined between the protective tube 10 and the inner tube 13.

The inner tube 13 has a narrowing or tapering part 16 nearer the outlet orifice, whereas the outer part retains its shape up to a short distance upstream of the orifice at 17, where the outer diameter of said outer part also decreases to provide a chamber in front of the end of the protective tube 10. The protective tube 10 includes a chamber outlet at its outer end in the form of a ring of outlet holes 18 for the water/air mixture. The orifice 19 of the outer narrowing part 16 of the inner tube carrying the powder/air suspension projects a short distance beyond the orifice part that includes the holes 18.

The through-passing holes 14 in the tube 13 are mutually of the same size and are disposed in a ring around the tube. Although this is a practical arrangement, the holes may alternatively be disposed in some other way provided that the effect achieved around the outlet hole 19 is generally uniform.

The narrowing inner part 16 is intended to function as a constriction to enable air in the inner tube 13 to exit more easily through the holes 14 and into the water channel 15. The wider channel 15 is intended to enable the mixture of air and water formed in said channel to expand readily.

Thus, in the case of the inventive embodiment the powder/air suspension is not required to entrain the water, and the air that entrains the water is delivered to the water channel and already mixed with the air in the channel 15 upstream of the outlet. The velocities of the powder/air suspension and the water/air mixture exiting from the surface treatment nozzle will lie within the same order of magnitude. For instance, the flow rate of the water/air mixture may be roughly 4–6 l/min. (instead of roughly 5–15 ml/min. with respect to solely water), and the flow rate of the powder/air suspension may be 15–20 l/min. The respective velocities of the powder/air suspension and the water/air mixture may be maintained in the same order of magnitude, by providing an appropriate balance between the different outlet areas 18/19, 22/23 and 27/28.

Figure 3:
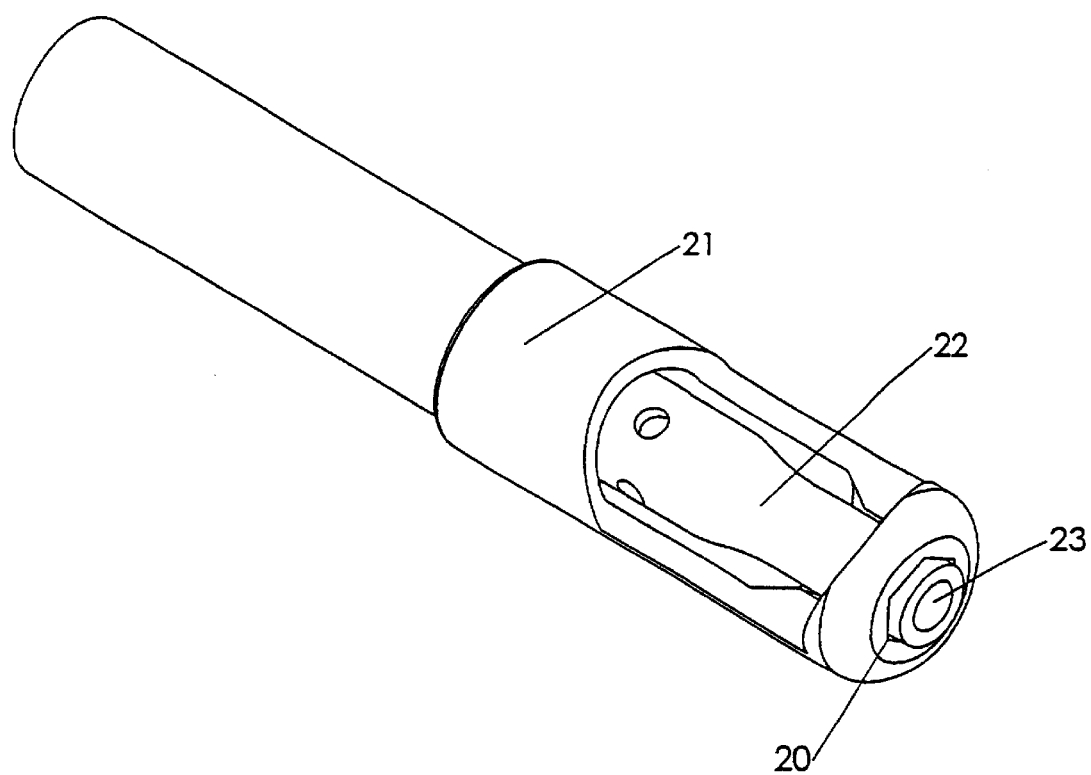
FIG. 3 illustrates in perspective and partially in section a second embodiment of a surface treatment head according to the invention.

Instead of a ring of holes around the orifice of the protective sleeve, the embodiment shown in FIG. 3 has an angular opening 20 from which the round tube of the narrowing part 17 projects. Although the illustrated opening 20 is shown to be hexagonal, it will be understood that the number of edges is can be chosen freely, the one proviso being that a water/air mist is able to exit from the region around the narrowing part 17. The opening may alternatively include outwardly extending arcs to facilitate exit of the water/air mixture. It is less expensive to provide only one opening in the end of the protective sleeve 21 than a plurality of holes. The orifice 17 is held in place by the sides of the opening 20, against which it supports.

In the case of the FIG. 3 embodiment, the water/air mixture is ejected through the generally triangular corner parts formed between the tube part 17 and the hole 20. This embodiment also includes a simpler variant of the restriction 22 in the inner tube than in the case of the arrangement shown in FIG. 1. The tube wall does not have different inner and outer diameters anywhere along its length, and narrowing of the tube has been achieved simply by compressing the tube externally. Although this embodiment results in a slightly lower velocity of the exiting water/air mixture, it is nevertheless fully acceptable.

Figure 4:
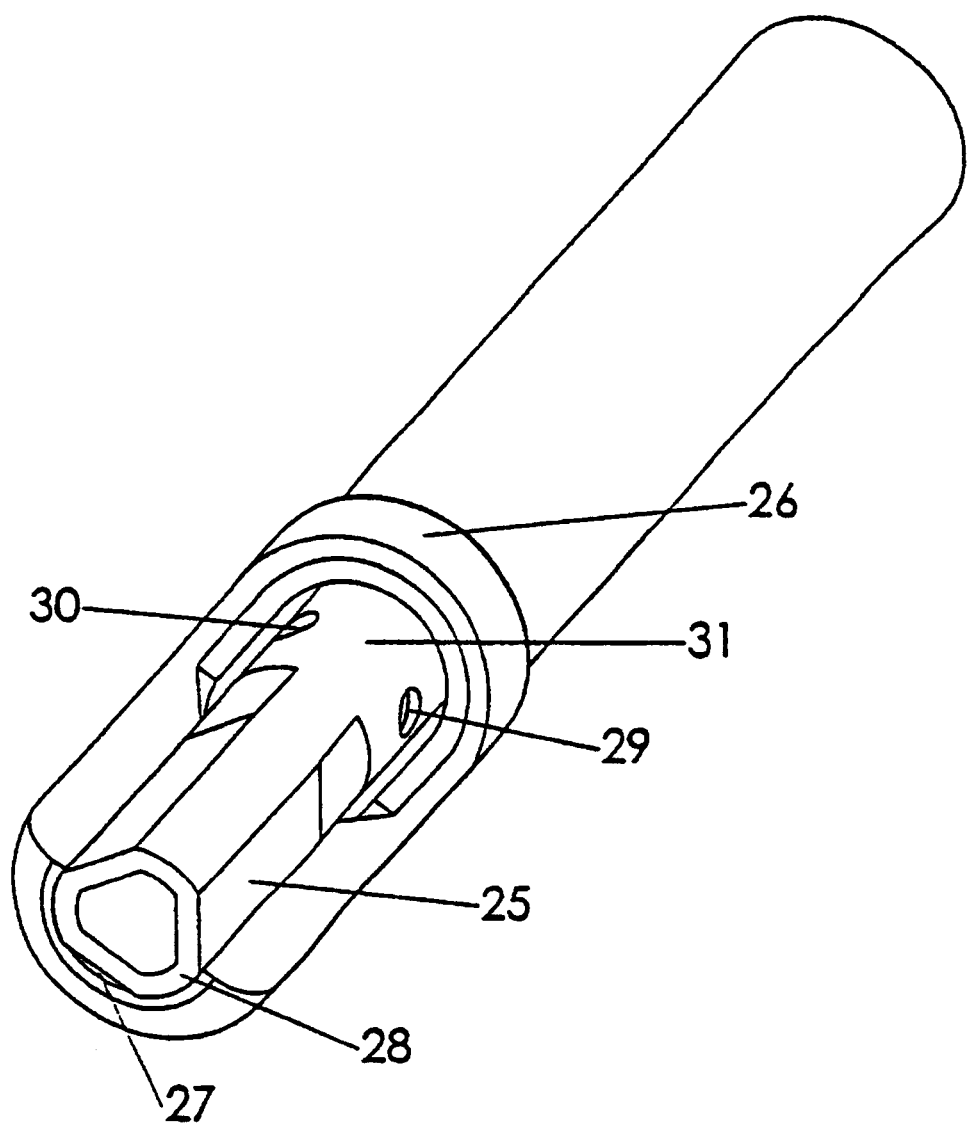
FIG. 4 illustrates in perspective and partially in section a third embodiment of the surface treatment head according to the invention.

FIG. 4 illustrates an embodiment in which the narrowing part 25 has been compressed to obtain an approximate polygonal shape (exaggerated in the drawing), which is particularly purposeful up to the orifice. Although the polygonal shape in this embodiment is shown to be triangular, it may alternatively be square, pentagonal or hexagonal and still function well.

The outlet opening 27 in the end of the protective tube 26 is round, which is easiest to form in a stainless steel protective tube, stainless steel being a preferred material in this context. In the case of the illustrated embodiment, the generally triangular orifice 28, preferably with rounded corners, is inserted so that its corners support against the side of the round opening 27. The powder/air suspension flows out through the opening on the orifice 28, whereas the water/air mixture flows out in the three segmental openings defined between the opening 27 and the orifice 28. The outlet openings 29, 30 for the air in the inner tube 31 are placed in line with each respective segmental opening parallel with the axis of the polishing nozzle. The embodiment shown in FIG. 4 has only one outlet opening on the tube 31 for each segmental opening, although more outlet openings may, of course, be placed symmetrically in relation to respective openings at said orifice. In the embodiment shown in FIG. 4, the triangular outlet opening for powder/air lies level with the opening 27. It will be obvious that the triangular orifice 28 may be displaced forwards and that the forwardly displaced openings for powder/air in the aforedescribed embodiments may lie in line with the end of the polishing nozzle, similar to the FIG. 4 embodiment. Alternatively, the powder/air opening may be withdrawn relative to the end of the polishing nozzle. A protruding powder/air opening is preferred, however, since this results in the least risk of clogging in respect of the water/air flow.

The size of the holes 14 in the inner tube 13, 31 and the outlet openings 29, 30 respectively is relatively irrelevant. The powder has a particle size distribution of a bell curve and since the powder is carried by the air at a high velocity and because each particle has a certain weight, it has been found that should any powder at all exit through the air exit holes, this powder will only correspond to an insignificant percent of the smallest particles. On the other hand, the air will readily expand out through the holes, particularly as the inner restriction increases the counter-pressure in the inner tube and thus assists said expansion. Neither are the holes 14 and 29, 30 respectively in the inner tube particularly critical, although they should, however, be found relatively close to the inner constriction.

It is nevertheless important with respect to optimum efficiency that all holes and cavities in the nozzle balance one another.

It will be understood that many modifications are possible within the scope of the invention defined in the accompanying Claims. For instance, instead of holes in the side of the inner tube, there may be arranged a circular grating that is adapted to allow air to enter but not powder particles. Although the nozzle of the illustrated embodiments has been shown to include a protective sleeve, it is possible to produce the component parts of the protective sleeve in one piece with the concentric tubes. However, the protective sleeve enables simple manufacture, because it can be produced in one piece and sealingly fastened to the outer tube 11. The tube 11 can be readily cut off at the beginning of the expansion channel. Holes 14 and 29, 30 can also be readily formed, as can also the constriction in at least the embodiments shown in FIGS. 3 and 4, including the design of the orifices 19, 23 and 28.

What is claimed is:

1. A surface treatment nozzle for generating (a) a surface treatment jet that comprises a suspension of surface treatment material and gas and (b) a liquid-containing surrounding jet for preventing dusting, wherein the velocity of the surface treatment jet is great than the velocity of solely liquid, and wherein the surface treatment jet is conveyed in an inner tube (13; 31) and the liquid is conveyed in a channel (12) defined between the inner tube and a tube (11) that surrounds said inner tube concentrically, the nozzle further comprising a mixing arrangement (14, 15, 16; 22; 29, 30, 25) for mixing the liquid with gas upstream of a nozzle outlet and imparting to the liquid/gas mixture a velocity of the same order of magnitude as the velocity of the surface treatment jet at said outlet.

2. The surface treatment nozzle according to claim 1, wherein the mixing arrangement includes an internal outlet from the liquid conducting channel (12), and discharge means (14; 20, 30) for delivering a part of the gas in the surface treatment jet as gas to be mixed with the liquid in an amount such that the liquid/gas mixture will have the desired velocity.

3. The treatment nozzle according to claim 2, wherein the mixing arrangement includes a liquid/gas mixture expansion channel (15) external of said discharge means.

4. The surface treatment nozzle according to claim 2, wherein the mixing arrangement includes an at least internal constriction (16; 25) in said inner tube downstream of the discharge means (14; 29,30).

5. The surface treatment nozzle according to claim 2, wherein the inner tube (13; 31) is circular at least at the nozzle outlet and has a diameter which provides space for a surrounding flow of liquid/gas mixture through an apertured (18; 20) area around the orifice (19; 23) of the inner tube.

6. The surface treatment nozzle according to claim 5, wherein the apertured area around the inner tube orifice (19) has the form of a ring of drilled holes (18).

7. The surface treatment nozzle according to claim 5, wherein the apertured area around the inner tube orifice (23) has the form of a central irregular but symmetrical hole (20) that includes wall parts which give internal support to the orifice (23) of the inner tube.

8. The surface treatment nozzle according to claim 2, wherein the inner tube (13; 31) carrying the suspension of surface treatment material and gas has at least at the outlet a generally polygonal orifice (28) containing plural corners and the orifice has a central round hole (27) whose diameter is adapted to support the corners and therewith provide space for a surrounding flow of liquid/gas mixture through apertures around the inner tube orifice (28).

9. The surface treatment nozzle according to claim 2, wherein the sizes and forms of the discharge means, the expansion channel, the inner constriction and the apertures for the outlet of the liquid/gas mixture are balanced relative to one another to provide the same order of magnitude between the velocities of the suspension of surface treatment material and gas and the liquid/gas mixture.

10. The surface treatment nozzle according to claim 1, wherein the gas is air and the surface treatment material is a polishing material.

11. A surface treatment nozzle for generating a surface treatment jet that includes a suspension of surface treatment material in a gas and separates a liquid-containing jet that surrounds the surface treatment jet, the nozzle comprising:

an inner tube conveying the suspension of the surface treatment material in the gas;

an outer tube surrounding said inner tube and defining a channel between said inner and outer tubes, a liquid for the liquid-containing jet being conveyed through the channel, wherein a velocity of the liquid in the channel is less than a velocity of the suspension conveyed through said inner tube;

an outlet for the surface treatment jet and the separate liquid-containing jet that surrounds the surface treatment jet; and mixing means for mixing the liquid from the channel with the gas from the inner tube upstream of said outlet and for imparting to the mixture of the liquid and the gas a velocity of the same order of magnitude as the velocity of the surface treatment jet at said outlet.

12. The nozzle of claim 11, wherein said mixing means comprises an opening through a wall of said inner tube and a constriction inside side inner tube downstream of said opening.

13. The nozzle of claim 11, wherein said outlet comprises a central opening through which the surface treatment jet is expelled and plural holes around said central opening through which the liquid-containing jet is expelled, said central opening communication with an interior of said inner tube and said plural holes communicating with an exterior of said inner tube.

14. The nozzle of claim 11, wherein said outlet comprises a central opening through which the surface treatment jet is expelled and polygonal opening around said central opening through which the liquid-containing jet is expelled, wherein walls of said polygonal opening support said inner tube at said outlet, said central opening communication with an interior of said inner tube and said polygonal opening communicating with an exterior of said inner tube.

* * * * *